United States Patent [19]
Senger et al.

[11] Patent Number: 5,866,127
[45] Date of Patent: Feb. 2, 1999

[54] VASCULAR PERMEABILITY FACTOR TARGETED COMPOUNDS

[75] Inventors: Donald R. Senger, Medfield; Harold F. Dvorak, Newton, both of Mass.

[73] Assignee: Beth Israel Deaconess Medical Center, Boston, Mass.

[21] Appl. No.: 464,956

[22] Filed: Jun. 5, 1995

Related U.S. Application Data

[63] Continuation of Ser. No. 327,709, Oct. 24, 1994, Pat. No. 5,659,013, which is a continuation of Ser. No. 779,384, Oct. 18, 1991, abandoned.

[51] Int. Cl.⁶ .......................... A61K 39/395; C07K 16/28; C07K 16/18
[52] U.S. Cl. ...................................... 424/178.1; 424/181.1; 424/183.1; 530/391.1; 530/391.3; 530/391.7
[58] Field of Search ............................. 424/178.1, 181.1, 424/183.1; 530/391.1, 391.3, 396.7

[56] References Cited

U.S. PATENT DOCUMENTS 4,456,550 6/1984 Dvorak et al. .
5,036,003 7/1991 Olander et al. .

FOREIGN PATENT DOCUMENTS 9102058 2/1991 WIPO .

OTHER PUBLICATIONS

Barth et al., 1990 *Scientific American*, 263:100 (Oct. 1990).
Bikfalvi et al., *J. Cell. Physiol.*, 149:50–59 (1991).
Connelly et al., *J. Biol. Chem.*, 264:20017–20024 (1989).
Connelly et al., *J. Clin. Invest*, 84;1470–1478 (1989).
Ferrara et al., *Biochem. Biophys. Res. Comm.*, 161:851–858 (1989).
Goodman et al., *Neurosurgery*, 24:701–708 (1989).
Itoh et al., *Cancer Immunol. Immunotherapy*, 32:88–94 (1990).
Keck et al., *Science*, 246:1309–1313 (1989).
Leung et al., *Science*, 246:1306–1309 (1989).
Myoken et al., *Proc. Nat'l Acad. Sci.*, 88:5819–5823 (1991).
Pastan et al., *Cell*, 47:641–648 (1986).
Rosenblum et al., *Cancer Communications*, 3(1):21–27 (1991).
Senger et al., *Cancer Res.*, 50:1774–1778 (1990).
Senger et al. *Science*, 219:983–985 (1983).
Tischer et al., *J. Biol Chem.*, 266:11947–11954 (1991).
Vaisman et al., *J. Biol. Chem.*, 265:19461–19466 (1990).
Vitetta et al., *Science*, 238:1098–1104 (1987).
Waldman, *Science*, 252:1657–1662 (1991).
Harris, TibTech v. 1 pp. 42,–44, 1993.

*Primary Examiner*—Toni R. Scheiner
*Assistant Examiner*—Nancy A. Johnson
*Attorney, Agent, or Firm*—David Prashker

[57] ABSTRACT

New compounds that bind specifically to vascular permeability factor (VPF) are used in methods of targeting these compounds, which include effector molecules that are, e.g., toxic, radioactive, or serve as marker labels, for tumor cells and the associated blood vessel endothelial cells, based on the discovery that VPF concentrates selectively in the endothelium and basement membrane lining tumor-associated blood vessels to a far greater degree than in normal vessels. By targeting VPF rather than the tumor cells themselves, the invention avoids the problems of tumor heterogeneity and diffusion distance.

6 Claims, 2 Drawing Sheets

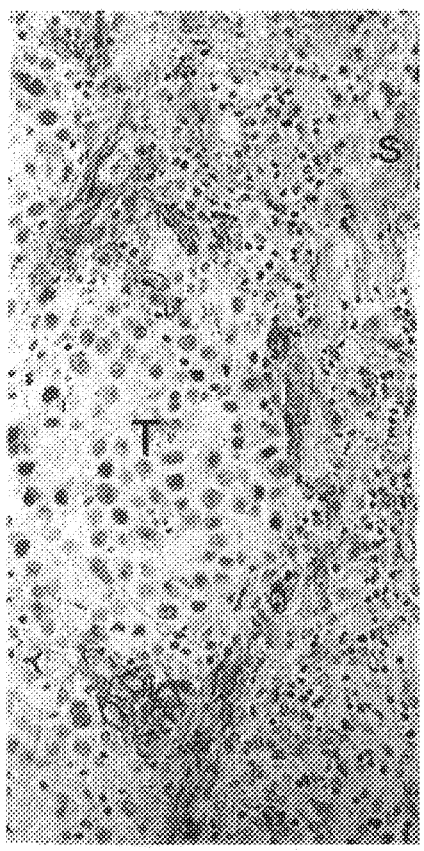
FIG. IA
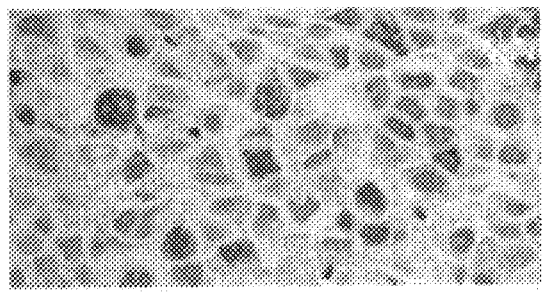
FIG. IB
FIG. IC
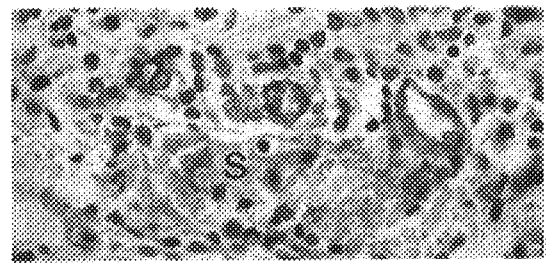
FIG. ID
FIG.IE
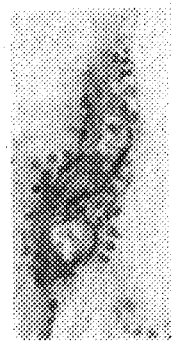
FIG.IF
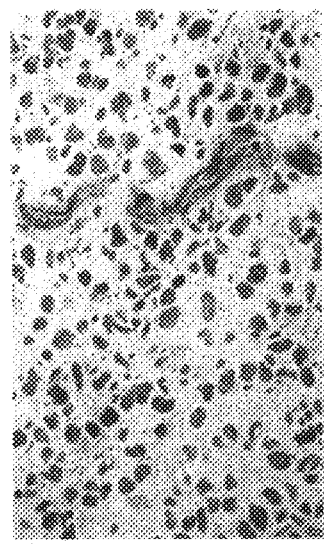
FIG.IG
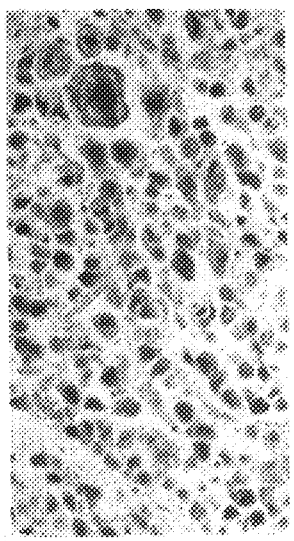
FIG.IH
FIG.II

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
( A ) LENGTH: 25
( B ) TYPE: amino acid
( D ) TOPOLOGY: linear -continued ( x i ) SEQUENCE DESCRIPTION: SEQ ID NO: 1:

Ala Pro Met Ala Glu Gly Glu Gln Lys Pro Arg Glu Val Val Lys Phe
                  5                   10                  15

Met Asp Val Tyr Lys Arg Ser Tyr Cys
                20              25

( 2 ) INFORMATION FOR SEQ ID NO: 2:

( i ) SEQUENCE CHARACTERISTICS:
        ( A ) LENGTH: 18
        ( B ) TYPE: amino acid
        ( D ) TOPOLOGY: linear ( x i ) SEQUENCE DESCRIPTION: SEQ ID NO: 2:

Cys Glu Cys Arg Pro Lys Lys Asp Arg Ala Arg Gln Glu Lys Lys Ser
                  5                   10                  15

Val Arg ( 2 ) INFORMATION FOR SEQ ID NO: 3:

( i ) SEQUENCE CHARACTERISTICS:
        ( A ) LENGTH: 26
        ( B ) TYPE: amino acid
        ( D ) TOPOLOGY: linear ( x i ) SEQUENCE DESCRIPTION: SEQ ID NO: 3:

Ala Pro Met Ala Glu Gly Gly Gly Gln Asn His His Glu Val Val Lys
                  5                   10                  15

Phe Met Asp Val Tyr Gln Arg Ser Tyr Cys
                20              25

( 2 ) INFORMATION FOR SEQ ID NO: 4:

( i ) SEQUENCE CHARACTERISTICS:
        ( A ) LENGTH: 26
        ( B ) TYPE: amino acid
        ( D ) TOPOLOGY: linear ( x i ) SEQUENCE DESCRIPTION: SEQ ID NO: 4:

Ala Pro Met Ala Glu Gly Gly Gly Gln Asn His His Glu Val Val Lys
                  5                   10                  15

Phe Met Asp Val Tyr Gln Arg Ser Tyr Cys
                20              25

VASCULAR PERMEABILITY FACTOR TARGETED COMPOUNDS

This is a continuation of application Ser. No. 08/327,709, filed Oct. 24, 1994, now U.S. Pat. No. 5,659,013 which is a continuation of application Ser. No. 07/779,384, filed Oct. 18, 1991, now allowed

BACKGROUND OF THE INVENTION

This invention relates to compounds that are specifically targeted for tumor cells and tumor-associated blood vessels and that can deliver various effector molecules to these sites.

Certain proteins are known to increase the permeability of blood vessels. One such protein factor, known as vascular permeability factor (VPF), is a highly conserved 34–42 kD protein secreted by many tumor cells that has been isolated from serum-free culture medium of carcinoma and sarcoma tumor cells and from tumor ascites fluids. Antibodies directed against VPF have also been created. Dvorak et al., U.S. Pat. No. 4,456,550, which is incorporated herein by reference, describes both the isolation of VPF and the creation of antibodies against VPF.

VPF is now known to be the same molecule as vascular endothelial growth factor (VEGF), as evidenced by the following points of identity: (1) molecular weight and $NH_2$—terminal amino acid sequence of the purified proteins (Ferrara, N., et al., *Biochem. Biophys. Res. Comm.*, 161:851–858 (1989); Connolly, D. T., et al., *J. Biol. Chem.*, 264: 20017–20024 (1989); Senger, et al., *Cancer Res.*, 50: 1774–1778 (1990)), (2) cDNA cloning and sequencing (Leung, D. W., et al., *Science*, 246:1306–1309 (1989); Keck, P. J., et al., *Science*, 246:1309–1312 (1989)), and (3) probable identical biological activities (Connolly, D. T., et al., *J. Clin. Invest.*, 84:1470–1478 (1989)).

Alternative forms of VPF/VEGF have been identified, and it has been determined that these forms arise as a consequence of alternative mRNA splicing of transcripts from the VPF/VEGF gene. Tischer, E., et al., *J. Biol. Chem.*, 266:11947–11954 (1991). As used herein, "VPF" encompasses all such alternative forms.

SUMMARY OF THE INVENTION

The inventors have discovered that VPF concentrates selectively in the endothelium and basement membrane lining tumor-associated blood vessels to a far greater degree than in normal vessels. This discovery permits the therapeutic use of new compounds that bind specifically to VPF, which compounds include a first, VPF-binding portion bonded to a second, effector portion, which is toxic, radioactive, or which serves as a label for tumor cells and the associated blood vessels. By targeting VPF rather than the tumor cells themselves, the invention avoids the problem of tumor heterogeneity, i.e., the limitation of antibody-based cancer therapies that target only a single type of tumor cell in a tumor containing multiple cell types. Furthermore, the invention avoids the problem of long diffusion distances often associated with other forms of therapy, e.g., those using monoclonal antibodies directed to the malignant cells of a certain tumor, by limiting the diffusion distance to a single cell layer—the endothelial cell itself. The compounds of the invention are particularly well suited for intravenous administration because they are targeted to the endothelial cells of the blood vessels. "Tumor-associated blood vessels" are those blood vessels, both preexisting and those newly induced by tumor angiogenesis, that are immediately adjacent to tumor cells, i.e., are within about 0.5 mm of tumor tissue. "Bind specifically" means that the compound does not substantially bind to any cell receptors or cell surface proteins in the body other than VPF.

In preferred embodiments, the first portion of the compound of the invention includes all or a specific binding portion of an antibody specific for VPF. An antibody specific for VPF may bind specifically to the entire VPF molecule or a portion thereof. Alternatively, the domain of the VPF receptor that causes it to selectively bind to VPF, once it has been identified, may itself be used as the first portion of the compound of the invention.

Where the compound is to be used therapeutically to destroy blood vessels supplying a tumor or the tumor cells themselves, which also contain VPF, the second, effector portion may include a toxin, preferably a cytotoxin, which may be a fragment of a peptide toxin which is enzymatically active but which does not possess generalized eukaryotic receptor binding activity. For example, the compound may contain fragment A of diphtheria toxin and enough of fragment B of diphtheria toxin to form a pore in a blood vessel endothelial cell membrane, but not enough of fragment B to cause generalized cell binding. The toxin may also be a metabolic disrupter, which is a molecule, e.g., an enzyme or a cytokine, that changes the metabolism of a cell such that its normal function is altered.

In further embodiments, the cytotoxin effector portion may be cholera toxin, ricin, 0-Shiga-like toxin (SLT-I, SLT-II, SLT-II$_V$), LT toxin; C3 toxin, Shiga toxin, pertussis toxin, tetanus toxin, Pseudomonas exotoxin, alorin, saponin, modeccin, gelanin, tumor necrosis factor alpha (TNF-α), lymphotoxin (LT), or calicheamicin.

The toxin effector portion can also be a radioactive molecule or a precursor thereof, e.g., a stable boron isotope for use in so-called "boron neutron capture therapy" to treat tumors. The radioactive molecule may also be any alpha particle emitter such as the radionuclides $^{211}$At, $^{212}$Pb, and $^{212}$Bi.

In another embodiment of the invention, the effector portion of the compound may also be a detectable label such as a radioactive molecule, where the compound is to be used for tumor imaging rather than therapy.

The compounds of the invention can be used in a method for delivering an effector molecule to the tumor-associated blood vessel endothelium or a tumor in a patient, by systemically administering to the patient a composition that includes one of the compounds of the invention in an excipient or pharmaceutically acceptable carrier, e.g., saline.

The invention also features a method of treating a tumor in a patient by systemically administering to the patient, e.g., intravenously, an effective amount of a composition including one of the compounds of the invention in an excipient, wherein the effector portion inhibits the proliferation of the tumor cells. "Inhibits proliferation of tumor cells" means that the effector portion of the compound kills or interferes with the proliferation of the cells of either or both of the tumor and the tumor-associated blood vessels, e.g., brings about infarction, thrombosis, or perforation of the blood vessels. By destroying the endothelial cells of the tumor-associated blood vessels that feed the tumor, the tumor itself is prevented from growing.

The first and second portions of the compound can be produced separately and joined together covalently, or they can be encoded by a fusion recombinant DNA molecule and joined by a peptide bond.

In another feature of the invention, the therapeutic compound is an antibody that is both capable of binding specifically to VPF and fixing complement, so that lysis of blood vessel endothelial cells is accomplished without need for an effector portion.

Other features and advantages of the invention will be apparent from the description of the preferred embodiments, and from the claims.

DETAILED DESCRIPTION

The drawings will first briefly be described. Drawings

FIGS. 1A, 1B, 1C, 1D, 1E, 1F, 1G, and 1I are photomicrographs showing the staining of tumor cells and tumor-associated blood vessel cells.

Figure 2A:
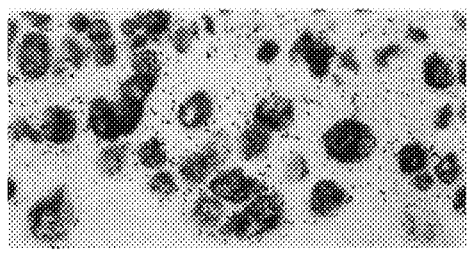
Figure 2B:
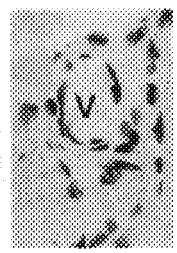
Figure 2C:
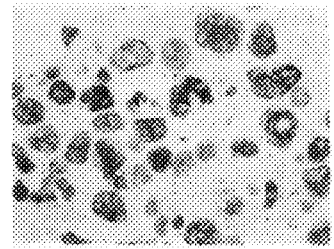

FIGS. 2A, 2B, and 2C are autoradiographs representing in situ hybridization of tumor cells with probes to guinea pig VPF mRNA.

VASCULAR PERMEABILITY FACTOR CONCENTRATES IN TUMORS AND TUMOR-ASSOCIATED BLOOD VESSELS

We have found that antibodies directed against synthetic peptides corresponding to N-terminal and internal sequences of VPF stained not just guinea pig and human tumor cells, but also the endothelial cells of immediately adjacent blood vessels. VPF staining was evident in adjacent preexisting venules and small veins as early as five hours after the tumor was transplanted, and reached a plateau in newly induced tumor vessels by about five days. We also found that VPF-stained vessels were hyperpermeable to macromolecules. In contrast, vessels more than about 0.5 mm away from the tumors were not hyperpermeable and were not significantly stained by the VPF antibodies.

Immunohistochemistry and In Situ Hybridization

Guinea pig tissues were fixed in formalin or carbodiimide and embedded in paraffin. Fresh frozen sections of human tumors were fixed in acetone. Immunohistochemistry was performed on 5–7 µm paraffin or frozen sections, using affinity purified first antibodies to guinea pig or human VPF peptides (see discussion below) and an avidin-biotin peroxidase procedure, slightly modified as described below. Controls included substitution of the first antibody with an unrelated rabbit antipeptide antibody, preabsorption of first antibody with specific peptide, and on-the-slide competition for first antibody with specific peptide.

Immunchistochemistry method

The procedure is carried out as follows. Deparaffinize tissues in xylene A,B,C in three 5 minute changes. Rehydrate with absolute alcohol for two 3 minute changes, 95% alcohol for one 3 minute wash, and with distilled water for one 5 minute wash. Incubate for 20 min. @ 37° C. with prewarmed Trypsin 2× (50 mg. Trypsin, 274 mg. $CaCl^2$, 200 ml tris buffer). Wash in tap water for 10 min. Wash in endogenous peroxidase blocking reagent for in 10 minutes (3 ml 30% $H_2O_2$+147 ml MeOH). Rinse in tape water for 10 min. Wash in blocking serum—5% normal goat serum in Tris buffer for 20 min. Wipe excess serum from slide. Place 2 drops of the first antibody (Ab) (first Ab+950 µl (10 ml Tris buffer, 29 mg. L-lysine, 250 mg NaCl)+50 µl goat serum, 1:50) on tissue, place slide in a covered moist chamber, and incubate 60 min. Dunk slide in Tris/PBS. Wash in 2% goat serum/Tris buffer, 2.5% NaCl three times for 5 min. each. Add biotinylated second Ab (4.75 ml (10 ml Tris buffer, 29 mg. L-lysine, 250 mg NaCl), 250 µl guinea pig serum, 20 µl second Ab) for a 30 min. incubation. Dunk in Tris/PBS; wash in 2% goat serum/Tris buffer, 2.5% NaCl for three 5 min. washes. Incubate in Vectastain ABC Reagent for 30 min. Dunk in Tris/PBS; wash in 2% goat serum/Tris buffer, 2.5% NaCl for three 5 min. washes. Wipe excess fluid from slide and apply 50 µl DAB working solution (under hood). Allow 3 minutes for color reaction to develop. Rinse in tap water. Rinse in distilled water. Wash in tap water for 3 min. Wash in 0.5% cupric sulfate for 5 min. Rinse in tap water for 3 min. Counterstain in Mayer's Hematoxylin for 20 to 30 sec. Rinse in tap water for 1 min. Rinse in warm tap water for 10 minutes. Dehydrate with 95% alcohol for a 3 min. wash, and with absolute alcohol for two 3 min. changes. Clear in xylene I, II, III for 5 min. each and mount in Permount.

In situ hybridization was performed using [$^{35}$S] labeled single-stranded RNA probes prepared by in vitro transcription of a 204 bp guinea pig VPF cDNA fragment to which had been added short flanking sequences containing HindIII and EcoRI restriction sites prior to cloning in pGem3Zf(+).

Localization of VPF in Tumors

Initial immunohistochemical studies were performed on growing, 5–8 day solid tumors. Ascites of chemically induced guinea pig line 1 and line 10 bile duct carcinomas were passaged in the peritoneal cavities of inbred strain 2 guinea pigs. To form solid tumors, 3×10$^6$ washed ascites tumor cells were injected subcutaneously into 400 g strain 2 guinea pigs. Dvorak et al., *J. Immunol.*, 122:166 (1979). To identify leaky blood vessels, colloidal carbon was injected i.v. 30 min. prior to tumor harvest. Dvorak et al., *J. Pathol.*, 133:95 (1988). Autochthonous human tumors were obtained following surgery.

Antibodies to VPF peptide 1A (APMAEGEQKPPEVVKFMDV-YKRSYC) (SEQ ID NO:1) stained only a minority of line 1 and line 10 tumor cell (FIG. 1A, B), but antibodies to peptide 6 (CECRPKKDRAR-QEKKSVR) (SEQ ID NO:2) strongly stained virtually all tumor cells (Fig. 1H). These findings suggest that VPF is abundantly present in nearly all line 10 tumor cells; the relatively poor staining of tumor cells with antibodies to the VPF N-terminus probably represents failure of fixation to preserve tumor cell cytoplasmic VPF in a conformation accessible to this antibody.

The new blood vessels induced by both tumors stained consistently and intensely with antibodies to VPF peptides 1A and 6 (FIG. 1). Vessel staining was circumferential and involved endothelial cells (EC) and vascular basement membranes; sometimes, adjacent extracellular matrix also stained weakly (FIG. 1A, D). Line 1 tumors underwent cell-mediated immune rejection, as described in Nagy et al., *Biochim. Biophys. Acta.*, 948:305 (1988), which was accompanied by a striking and rapid (within 24–48 h) loss of vessel staining (not shown). The rapid depletion of VPF that accompanied tumor destruction suggests rapid turnover of blood vessel-associated VPF.

Studies with affinity purified antibodies to VPF peptide 1B (APMAEGGGQNHHEVVKFMDVYQRSYC)(SEQ ID NO:3) indicate that blood vessels associated with human tumors also exhibit VPF staining and in a pattern identical to that of the guinea pig tumors (FIG. 1G).

In particular, as shown in FIG. 1. the immunohistochemistry of line 10 (A–C, E, F, H, I) and line 1 (D) guinea pig bile duct carcinomas and a human large cell lymphoma (G) is demonstrated with antibodies directed against guinea pig or human VPF peptides: A–F, peptide 1A; G, peptide 1B; H, I peptide 6. The immunohistochemical reaction product appears yellow-brown. FIG. 1A. shows an overview showing minimal staining of line 10 tumor cells (T) with antibody to peptide 1A but intense staining of tumor-associated blood vessels 8 days following transplant. Focally, adjacent stroma (s) is also stained. FIGS. 1B–1D are higher magnification photographs illustrating variable line 10 tumor cell staining (b) and intense staining of line 10 (C) and line 1 (D) tumor vessels. FIG. 1E shows that new ascites tumor-induced blood vessels, of the peritoneal wall stain intensely, whereas attached tumor cells (arrow) are unstained (PC=peritoneal cavity). FIG. 1F shows that preexisting venules of normal skeletal muscle adjacent to a line 10 tumor are strongly stained with antibody to peptide 1A. FIG. 1G shows that vessels in a human B cell lymphoma react strongly with antibody to peptide 1FIGS. 1H and 1I shows the staining of nearly all line 10 tumor cells (H) and a nearby venule (arrow in I) with antibodies to peptide 6. As with antibodies to the VPF N-terminus, adjacent venules and small veins (arrow in I) stain intensely but arteries (a in I) stain faintly or not at all (SEQ ID NO:1). The magnifications in FIG. 1 are: A, ×245; B and D, ×405; C, ×313; E, F, and H, ×260; G, ×320; and I, ×410.

In addition to the tumor microvasculature, vessels coursing through immediately adjacent normal tissues also exhibited specific VPF antibody staining (FIG. 1F). Immunoreactive vessels were venules and small veins immediately adjacent to the tumors, i.e., within about 0.5 mm of the tumors; arterioles, capillaries and vessels of any type at greater distances from tumor cells or in other tissues and organs exhibited no staining. Consistent with these findings, antibodies to VPF peptide 1A also stained immediately adjacent, preexisting host venules and small veins as early as 5 h after tumor cell transplant. These preexisting blood vessels, as well as the newly induced tumor vessels, were permeable as judged by their concentration of circulating colloidal carbon.

Employing in situ hybridization, nearly all line 10 tumor cells present in solid or ascites tumors reacted with the antisense RNA probe for guinea pig VPF mRNA (FIG. 2A, C). Tumor blood vessels were negative for VPF message (FIG. 2B), indicating that VPF is synthesized by tumor cells and not by EC; therefore, the VPF identified in tumor-associated vessels reflects selective binding of tumor cell-secreted VPF. The intense tumor vessel labeling observed with anti-VPF peptide antibodies was unexpected in that VPF exerts its effects on vascular endothelium at low nanomolar to subpicomolar concentrations, well below the levels of immunohistochemical detection. Thus, when VPF was injected into normal guinea pig skin in amounts sufficient to increase local vascular hyperpermeability greatly, VPF could not be demonstrated immunohistochemically. Therefore, VPF accumulates in the blood vessels around growing tumors in concentrations that are much greater than those necessary to trigger vascular responses.

In particular, FIGS. 2A–2C are autoradiographs representing in situ hybridization performed on paraffin sections of solid line 10 tumors with [$^{35}$S]-labelled antisense (A, B) and (C) RNA probes to guinea pig VPF MRNA. With antisense probes, labelling is observed over nearly all tumor cells (A) but not over adjacent microvessels (v in B). Autoradiograph exposure time in A were selected to permit clear visualization of cells underlying grains. With the corresponding sense probe (C), tumor cells are not labelled, even after lengthy exposures. The magnifications in FIG. 2 are: A, ×500; and B and C, ×385.

Compounds Useful in the Methods of the Invention

In general, there are two ways in which therapeutic compounds of the invention can act: (1) the compound can kill, or otherwise inhibit proliferation, of a blood vessel endothelial cell or tumor cell via toxicity of the effector molecule delivered to the endothelium of the tumor-associated vessel by the VPF-specific portion; and (2) the compound can be an antibody that can by itself cause cell lysis by inducing complement fixation. In both cases the compound must be targeted to VPF; this preferably is accomplished by employing an anti-VPF antibody or portion thereof as the first portion of the compound.

When an anti-VPF antibody is the targeting portion of the compound, a cytotoxic hybrid compound can be formed by fusing all or part of the antibody to a cytotoxin. The effectiveness of such an antibody/toxin hybrid is enhanced if the hybrid compound is taken up by cells to which it binds.

Compounds can be hybrid molecules formed by the fusion of all or part of two or more molecules. Such a hybrid compound can be a hybrid protein encoded by a recombinant DNA molecule, in which case the two portions are joined (directly or through an intermediary domain) by a peptide bond. Alternatively, the two portions can be produced separately and joined by a covalent bond in a separate chemical linkage step. In some cases, the cytotoxic portion of a hybrid compound may itself be derived from two separate molecules.

Antibodies as Targeting Agents

Antibodies directed against VPF can be used to direct toxins, or other effector molecules, to cells bearing VPF. The antibodies may be monoclonal or polyclonal, and can be derived from any suitable animal by standard techniques. The antibodies may be produced by using purified or recombinant VPF or peptide fragments thereof. Where the antibody is monoclonal and is intended for human therapy, humanized murine monoclonal antibodies are preferred, e.g., as described in Cabilly et al., U.S. Pat. No. 4,816,567, incorporated herein by reference.

The invention can employ not only intact monoclonal or polyclonal antibodies, but also an immunologically-active antibody fragment, for example, a Fab or (Fab)$_2$ fragment; an antibody heavy chain, an antibody light chain; a genetically engineered single-chain Fv molecule (Ladner et al., U.S. Pat. No. 4,946,778); or a chimeric antibody, for example, an antibody which contains the binding specificity of a murine antibody, but in which the remaining portions are of human origin.

These antibodies, or antibody fragments, can be fused to a cytotoxin either by virtue of the toxin and the antibody being encoded by a fused gene which encodes a hybrid protein molecule, or by means of a non-peptide covalent bond which is used to join separately produced antibody and toxin molecules. Several useful toxins are described below.

Antibodies to VPF

A method to prepare an antibody is as follows. Purified VPF protein (about 10 μg), in a polyacrylamide gel slice, prepared as described in Example I of U.S. Pat. No. 4,456,550, which is incorporated herein by reference, is homogenized (Dounce) in an equal volume of complete Freund's adjuvant (total volume about 5 ml). Animals, e.g., rabbits, are given intradermal injections on each side and on each leg below the knee and at four SC cites. Immunization is repeated 6 weeks after the initial immunization as described above, but incomplete Freund's adjuvant is used (without the mycobacterial component). Eleven weeks after initial immunization, 10 μg of purified VPF protein is extracted from polyacrylamide gel by homogenization in 2 ml phosphate buffered saline solution. The resulting extract is injected at two sites (1 ml at each site) in each animal.

The antibody is present in immunoglobulin (IG) purified from blood of rabbits so injected. Specifically, the serum IG is bound to a protein A sepharose column and the antibody is eluted with a high salt concentration or low-pH aqueous solution.

VPF Peptide Fragment Antibodies

Antibodies to peptide fragments of VPF are also suitable for use as the first portion of the compound of the invention. In addition, binding portions of such antibodies to all or segments of VPF are also suitable. One such antibody preparation was made as follows.

The N-terminal 25 amino acid sequence of guinea pig VPF, here designated peptide 1A and expressed in single letter code, is APMAEGEQKPREVVKFMDVYKRSYC. Senger et al., *Cancer Res.*, 50:1774 (1990). The 26 amino acid N-terminus of human VPF (peptide 1B) differs from that of guinea pig VPF by the six Underlined amino acids: APMAEGGGQNHHE-VVKFMDVYQRSYC. (SEQ ID NO:4) Keck et al., *Science*, 246:1309 (1989). These, and an internal peptide (CECRPKKDRARQEKKSVR, peptide 6(SEQ ID NO:2)) corresponding to amino acids 102 to 119 of the 189 amino acid form of human VPF (Keck et al., supra) were synthesized, coupled to a protein carrier, and used to immunize rabbits (Senger et al., supra).

Monoclonal Antibodies to VPF

Monoclonal antibodies useful in the compound of the invention can be made by immunizing mice with human VPF or VPF peptides 1A, 1B, or 6, supra, fusing the murine splenocytes with appropriate myeloma cells, and screening the antibodies produced by the resultant hybridoma lines for the requisite VPF binding properties by means of an ELISA assay. Antibody production and screening can be performed according to Uchiyama et al., *J. Immunol.*, 126:1393 (1981). Alternatively, useful antibodies may be isolated from a combinatorial library produced by the method of Huse et al., *Science*, 246:1275 (1989).

Toxins as the Effector Portion

The toxin molecules useful in the methods of the invention are preferably toxins, such as peptide toxins, which are significantly cytotoxic only when present intracellularly. The term toxin includes cytotoxins, metabolic disrupters (inhibitors and activators) that disrupt enzymatic activity and thereby kill blood vessel endothelial cells or occlude the blood vessels, and radioactive molecules that kill all cells within a defined radius of the effector portion. A metabolic disrupter is a molecule, e.g., an enzyme or a cytokine, that changes the metabolism of a cell such that its normal function is altered. Broadly, the term toxin also includes any effector that causes infarction of the tumor associated blood vessels.

Preferably, a peptide toxin is fused to the VPF binding portion of the compound by producing a recombinant DNA molecule that encodes a hybrid protein molecule. Such an approach ensures consistency of composition.

Many peptide toxins have a generalized eukaryotic receptor binding domain; in these instances the toxin must be modified to prevent intoxication of cells not bearing the targeted receptor (e.g., to prevent intoxication of cells not bearing the VPF but having a receptor for the unmodified toxin). Such modifications must be made in a manner that preserves the cytotoxic functions of the molecule. Potentially useful toxins include, but are not limited to: diphtheria toxin, cholera toxin, ricin, 0-Shiga-like toxin (SLT-I, SLT-II, SLT-II$_V$), LT toxin, C3 toxin, Shiga toxin, pertussis toxin, tetanus toxin, Pseudomonas exotoxin, alorin, saponin, modeccin, and gelanin.

Other toxins include tumor necrosis factor alpha (TNF-α) and lymphotoxin (LT). LT is another name for tumor necrosis factor beta (TNF-β), in contrast to classic tumor necrosis factor, which is now called TNF-α. Beutler, B., *Hosp Pract*, 25:45–56 (1990). TNF-α is primarily made by monocytes, whereas LT is produced by lymphocytes. Both are highly cytotoxic.

Another toxin useful as an effector in the compound of the invention is calicheamicin gamma 1I, a recently discovered diyne-ene containing antitumor antibiotic with considerable potency against murine tumors. In vitro, this drug interacts with double-helical DNA in the minor groove and causes site-specific double-stranded cleavage. The ability of calicheamicin gamma 1I to cause double-strand cuts at very low concentrations may account for its potent antitumor activity. Zein, N., et al., *Science*, 240:1198–201 (1988).

Diphtheria Toxin-based Molecules

As an example, diphtheria toxin can be used to produce molecules useful in the method of the invention. Diphtheria toxin, whose sequence is known, is described in detail in Murphy U.S. Pat. No. 4,675,382, which is incorporated herein by reference. The natural diphtheria toxin molecule secreted by *Corynebacterium dichtheriae* consists of several functional domains which can be characterized, starting at the amino terminal end of the molecule, as enzymatically-active Fragment A (amino acids Gly$_1$–Arg$_{193}$) and Fragment B (amino acids Ser$_{194}$–Ser$_{535}$), which includes a translocation domain and a generalized cell binding domain (amino acid residues 475 through 535).

Linkage of Toxins to Anti-VPF Antibodies

The antibody and the cytotoxin of useful hybrid compounds can be linked in any of several ways. If the compound is produced by expression of a fused gene, a peptide bond serves as the link between the cytotoxin and the antibody. Alternatively, the toxin and the antibody can be produced separately and later coupled by means of a non-peptide covalent bond.

For example, the covalent linkage may take the form of a disulfide bond. In this case, the DNA encoding this antibody can be engineered, by conventional methods, to contain an extra cysteine codon. The cysteine should be positioned so as to not interfere with the VPF binding activity of the compound.

For a disulfide bond linkage, the toxin molecule is also derivatized with a sulfhydryl group reactive with the cysteine of the modified antibody. In the case of a peptide toxin this can be accomplished by inserting a cysteine codon into the DNA sequence encoding the toxin. Alternatively, a sulfhydryl group, either by itself or as part of a cysteine residue, can be introduced using solid phase polypeptide techniques. For example, the introduction of sulfhydryl groups into peptides is described by Hiskey, *Peptides*, 3:137 (1981). Derivatization can also be carried out according to the method described for the derivatization of a peptide hormone in Bacha et al., U.S. Pat. No. 4,468,382, incorporated herein by reference. The introduction of sulfhydryl groups into proteins is described in Maasen et al., *Eur. J. Biochem.*, 134:32 (1983). Once the required sulfhydryl groups are present, the cytotoxin and the antibody are purified, both sulfur groups are reduced, cytotoxin and antibody are mixed (in a ratio of about 1:5 to 1:20), and disulfide bond formation is allowed to proceed to completion (generally 20 to 30 minutes) at room temperature. The mixture is then dialyzed against phosphate buffered saline to remove unreacted antibody and toxin molecules. Sephadex chromatography or the like is used to separate the desired toxin-antibody conjugate compounds from toxin-toxin and antibody-antibody conjugates on the basis of size.

Immune Response Modulators as the Effector Portion

The effector portion of the compounds of the invention may also be so-called modulators of the immune system that either activate or inhibit the body's immune system at the local level. For example, cytokines, e.g., lymphokines such as IL-2, delivered to the tumor-associated blood vessel endothelial cells can cause the proliferation of cytotoxic T-lymphocytes or natural killer cells in the vicinity of the tumor. As another example, certain activators delivered to the endothelial cells would activate those cells to express luminal surface tissue factor to produce a thrombus that can block the blood vessel. Other useable immune response modulators include IL-1 and interferon.

Radioactive Molecules as the Effector Portion

The effector portion of the compound of the invention may also be a radioactive molecule, e.g., a radionuclide, or a so-called sensitizer, e.g., a precursor molecule, that becomes radioactive under specific conditions, e.g., boron when exposed to a beam of low-energy neutrons in the so-called "boron neutron capture therapy" (BNCT). Barth et al., *Scientific American,* October 1990:100–107 (1990). The compounds of the invention with such radioactive effector portions may be used both to inhibit tumor cell proliferation and to label the tumor cells for imaging purposes.

Radionuclides are single atom radioactive molecules that can emit either $\alpha$, $\beta$, or $\gamma$ particles. Alpha particle emitters are preferred to $\beta$ or $\gamma$ particle emitters, because they release far higher energy emissions over a shorter distance, and are therefore efficient without significantly penetrating, and harming, normal tissues. Suitable a particle emitting radionuclides include $^{211}At$, $^{212}Pb$, and $^{212}Bi$.

The radioactive molecule must be must be tightly linked to the VPF antibody either directly or by a bifunctional chelate. This chelate must not allow elution and thus premature release of the radioactive molecule in vivo. Waldmann, *Science,* 252:1657–62 (1991).

Boron Neutron Capture Therapy

To adapt BNCT to the present invention, a stable isotope of boron, e.g., boron 10, is selected as the effector portion of the compound. The boron is delivered to and concentrates in the tumor cells and the tumor-associated blood vessel endothelial cells by the specific binding of the first portion of the compound to the VPF. After a time that allows a sufficient amount of the boron to accumulate, the tumor is imaged and irradiated with a beam of low-energy neutrons, e.g., about 0.025 eV.

This neutron irradiation, by itself, causes little damage to either the healthy tissue surrounding the tumor, or the tumor itself. However, when an atom of boron 10, e.g., in an endothelial or a tumor cell, captures one of these neutrons, an unstable isotope, boron 11, forms and instantly fissions yielding lithium 7 nuclei and energetic $\alpha$ particles, about 2.79 million eV. These heavy particles are a highly lethal, but very localized, form of radiation, because $\alpha$ particles have a path length of only about one cell diameter (10 microns).

Calculations have shown that to destroy a tumor cell, about one billion boron atoms are required along with a flow of thermal neutrons of from $10^{12}$ to $10^{13}$ neutrons per square centimeter, so that the radiation generated by the a particles exceeds the background radiation generated by neutron capture reactions with nitrogen and hydrogen.

Thermal neutrons present certain problems, e.g., they are rapidly attenuated and are therefore difficult to deliver to tumors located deep inside the body. Epithermal neutrons, on the other hand, penetrate, and therefore do not damage, tissue, better than thermal neutrons. However, reactors that produce such epithermal neutron beams are not yet readily available outside special university and research laboratories, such as the Brookhaven National Laboratory and the Massachusetts Institute of Technology. Certain radioisotopes, e.g., californium 252, can be used as an alternative source of neutrons.

Assays for Toxicity

Compounds of the invention (both antibodies and hybrid molecules) can be screened for the ability to inhibit the proliferation of tumor cells and tumor-associated blood vessel endothelial cells by means of an assay as described below.

Human tumors can be grown in athymic nude BALB/c mice by subcutaneous injection of $5 \times 10^6$ cells of any of the following human cell lines: MNNG—HOS (osteosarcoma), HeLa S3 (cervical carcinoma), COLO 205 (bowel carcinoma), WiDr (bowel carcinoma), HT1080 (fibrosarcoma), PA-1 (ovarian carcinoma). Senger, D. R., et al., *Cancer Res.,* 45:5818–5823 (1985).

This procedure results in tumors (palpable by 14 days) which grow progressively and kill the animal within 2 months if there is no intervention. The compounds of the invention can be tested by intravenous or intramuscular injection to determine their toxicity to the solid tumors. Significant shrinkage of the tumor compared to a control untreated tumor indicates toxicity. The compounds of the invention may be administered in dosages of 0.05–15.0 $\mu g/g$ in one or in a series of one injection per day for 5 or 10 days.

Therapy

Generally, the compounds of the invention are administered systemically as by intravenous infusion. Dosages of compounds useful in the methods of the invention will vary, depending on factors such as whether the substance is a cytotoxin or a lytic antibody. In the case of toxic molecules as the effector portion of the compound, the extent of cell uptake is an important factor; less permeable toxins must be administered at a higher dose. The compounds of the invention will generally be administered in a series, e.g., two to fifteen, more preferably five to ten doses, given, e.g., once or twice per day or every two or three days, or in a regular courses interrupted by periods of cessation of treatment. Preferable dosages will be in the range of 50–1000 $\mu g/kg$.

Other embodiments are within the following claims.

We claim:

1. A method for delivering a toxin effector molecule to a tumor-associated blood vessel in a patient comprising the step of:
    systemically administering to the patient a composition comprising
        a compound comprised of a first portion including at least the binding part of an antibody which binds specifically to vascular permeability factor (VPF) bound previously to a tumor-associated blood vessel, and a second effector portion covalently bonded to said first portion wherein said second effector portion comprises a toxin molecule; and
        an excipient.

2. A method of labeling a tumor-associated blood vessel in a patient comprising the step of:
    systemically administering to the patient a compound comprised of
        a first portion including at least the binding part of an antibody which binds specifically to vascular permeability factor (VPF) bound previously to a tumor-associated blood vessel, and
        a second effector portion covalently IV bonded to said first portion wherein said second effector portion comprises a detectable marker.

3. A method for delivering a toxin effector molecule to a tumor-associated blood vessel in a patient comprising the step of:
    systemically administering to the patient a compound comprised of
        a first portion including at least the binding part of an antibody which binds specifically to vascular permeability factor (VPF) bound previously to a tumor-associated blood vessel, and
        a second effector portion covalently bonded to said first portion wherein said second portion comprises a toxin molecule.

4. A method of labeling a tumor-associated blood vessel in a patient comprising the step of:

systemically administering to the patient a composition comprising
   a compound comprised of a first portion including at least the binding part of an antibody which binds specifically to vascular permeability factor (VPF) bound previously to a tumor-associated blood vessel and a second effector portion covalently bonded to said first portion wherein said second effector portion comprises a detectable marker; and
an excipient.

5. The method as recited in claim 1 or 3 wherein said toxin effector molecule is selected from the group consisting of cytotoxins, metabolic disrupters, radioactive molecules, infarction causing agents, peptide exotoxin, and DNA specific agents.

6. The method as recited in claim 2 or 4 wherein said detectable marker is a radionucleotide.

\* \* \* \* \*